(12) United States Patent
Lia et al.

(10) Patent No.: US 6,168,566 B1
(45) Date of Patent: Jan. 2, 2001

(54) PRESSURE SENSING DEVICE

(75) Inventors: Raymond A. Lia, Auburn; James M. Baxter, Jordan; Robert L. Vivenzio, Auburn, all of NY (US)

(73) Assignee: Welch Allyn, Inc., Skaneateles Falls, NY (US)

( * ) Notice: Under 35 U.S.C. 154(b), the term of this patent shall be extended for 0 days.

(21) Appl. No.: 09/172,552

(22) Filed: Oct. 14, 1998

(51) Int. Cl.$^7$ ........................................ A61B 5/00
(52) U.S. Cl. ...................... 600/488; 600/561; 73/700; 73/715
(58) Field of Search ................... 600/485, 486, 600/488, 561; 73/700, 715

(56) References Cited

U.S. PATENT DOCUMENTS

| 3,068,702 | 12/1962 | Saddock . |
|---|---|---|
| 3,990,306 | 11/1976 | Denis . |
| 4,036,061 | 7/1977 | Speidel . |
| 4,040,298 | 8/1977 | Lee et al. . |
| 4,109,535 | 8/1978 | Reed et al. . |
| 4,433,579 | 2/1984 | Horn . |
| 4,552,153 | 11/1985 | Newman et al. . |
| 4,685,336 | 8/1987 | Lee . |
| 4,733,564 | * 3/1988 | Gorge .................................. 73/715 |
| 5,181,422 | 1/1993 | Leonard et al. . |
| 5,189,979 | 3/1993 | Popenoe . |
| 5,438,874 | * 8/1995 | Hamma ................................ 73/715 |
| 5,665,921 | 9/1997 | Gerst et al. . |
| 5,712,428 | 1/1998 | Schleiferböck . |
| 5,753,821 | * 5/1998 | Chou .................................. 73/715 |
| 5,970,796 | * 10/1999 | Blake et al. .......................... 73/715 |

* cited by examiner

Primary Examiner—Robert L. Nasser
(74) Attorney, Agent, or Firm—Wall Marjama & Bilinski

(57) ABSTRACT

A pressure sensing device includes a housing having an interior sized for containing a flexible diaphragm, the deflection of which causes subsequent movement of a movement mechanism relative to an indicating dial face. The diaphragm is nonfixedly attached to the bottom side of a support plate disposed within the housing interior, in which the plate includes a center opening sized to support the movement mechanism and position an input member of the movement mechanism adjacently to the flexible diaphragm. A pressure chamber is established between the bottom of the housing and the diaphragm such that air or other fluid entering the chamber causes deflection of the diaphragm and subsequent movement of the input member. Preferably, the diaphragm is retained within a slot formed in the housing and clamped into contact with a flexible gasket and the bottom surface of the support plate.

16 Claims, 5 Drawing Sheets

PRESSURE SENSING DEVICE

FIELD OF THE INVENTION

The invention relates to the field of pressure sensing devices, and in particular to a pressure sensing device, such as a blood pressure gauge, utilizing a member for supporting an expandable diaphragm and the gauge movement mechanism.

BACKGROUND OF THE INVENTION

Pressure sensing devices are widely known, such as sphygmomanometers which include a pneumatic bulb used to inflate a pressure chamber of an attached sleeve or cuff that is fitted over the arm or leg of a patient. A bellows assembly, responsive to fluid changes of the pneumatic bulb and the sleeve pressure chamber is positioned in a dial indicator housing. The pointer of the dial indicator is interconnected to the bellows assembly by a movement mechanism of the gauge, whereby expansion of the bellows assembly causes a corresponding circumferential movement of the pointer.

Known designs of these devices require separate support plates for independently supporting the movement mechanism and the diaphragm, respectively, and defining an expansion chamber for the diaphragm therebetween. These designs require a maintained height dimension of the housing, making the development of a compact design difficult, at best.

Numerous changes have been effected concerning the movement mechanism of pressure sensing devices. In the past, these mechanisms were intricate and precise and were akin in their manufacture and precision to Swiss watches. For example, in one such mechanism, a pair of diaphragm springs are attached adjacent opposite ends of a spindle. A bottom end of the spindle is placed in contact with the inflatable bellows assembly and a twisted bronze band perpendicularly disposed at the top end of the spindle is connected thereto by a horizontally disposed spring bent part. As the spindle axially deflects due to the inflation of the bellows assembly, the bent spring part is caused to deflect and the band twists. The twisting of the bronze band causes corresponding rotation of a pointer relative to an adjacent dial indicating face.

Movement mechanisms, such as the preceding, involve a plurality of moving components, each having multiple bearing surfaces. As a consequence, significant tolerancing is required in their assembly.

A more simplified movement mechanism design is described, for example, in copending and commonly assigned U.S. Ser. No. 08/972,573, filed Nov. 18, 1997, which utilizes a vertically disposed linear cartridge including a spirally wrapped ribbon spring having one end mounted to an axially movable elongate pin and a remaining end attached to a cap member fixed to the cartridge. A bottom portion of the pin is positioned relative to the expandable diaphragm, wherein subsequent axial translation of the pin elongates the spirally wound ribbon member and produces repeatable circumferential movement of a needle or pointer element supported at the top end of the pin relative to the dial indicator face.

Though the manufacture of a pressure sensing device is considerably simplified utilizing the above movement mechanism design, there have been to date no efforts made to simplify the manufacture of the device relative to the support of the diaphragm and/or the interaction between the deflection of the diaphragm and the movement mechanism of the gauge.

SUMMARY OF THE INVENTION

It is therefore a primary object of the present invention to improve the state of the art of pressure sensing devices.

It is a further primary object of the present invention to provide a pressure sensing device, such as a blood pressure gauge, which can be lighter in weight than previously known sensing devices.

It is yet a further primary object of the present invention to provide a pressure sensing device having improved features with regard to the assembly and support of the bellows assembly and the movement mechanism.

Therefore and according to a preferred aspect of the present invention, a pressure sensing device is provided comprising:

a housing having a hollow interior and including at least one inlet disposed in a lower portion thereof;

a source of fluid in communication with said at least one inlet;

a flexible diaphragm adjacently disposed relative to said at least one inlet, said diaphragm having a surface which is responsive to the flow of fluid entering and leaving said housing through said at least one inlet;

a movement mechanism having an input member disposed adjacently to the flexible expanding surface of said diaphragm and an outlet member attached to indicating means in an upper portion of said housing; and means for supporting said flexible diaphragm and said movement mechanism within the interior of said housing, said supporting means including a common support plate having a bottom side and a top side, wherein said diaphragm is disposed adjacent the bottom side of said support plate, and wherein the lower part of said housing and said support plate define a pressure chamber sized for allowing deflection of said diaphragm.

Preferably, the common support plate includes a center opening sized for retaining one end of the movement mechanism and includes means for positioning the input element relative to the deflecting surface of the diaphragm.

A feature of the present invention is that the support plate is substantially circular in shape and includes a plurality of ears which engage tabs provided in the circumferential inner wall of the housing using a bayonet type of connection.

Another feature of the invention is that a flexible gasket, such as an O-ring, is provided between the support plate and the outer edge of the diaphragm. The flexible gasket seals the outer edge of the diaphragm relative to the bottom of the housing and also provides increased linearity and repeatability, as opposed to conventional pressure sensing device gauge designs requiring two or more support plates.

Yet another feature of the present invention is that positioning the diaphragm on the interior side of a common support plate allows the pressure chamber to be established between the housing interior and the support plate. Moreover, a common support plate also fixedly supports the movement mechanism, in the manner of prior bridge plate assemblies, and suitably positions an input member of the mechanism relative to the deflecting diaphragm. By inverting the diaphragm against the bottom of the single support plate, all required functions previously requiring at least two support plates are accomplished. Preferably, the walls of the housing are made from a flexible plastic material to allow minor flexing thereof due to the presence of entering air.

Alternatively, and depending on the design of the gauge housing, a separate intermediate structure or adapter can be interposed between the support plate and the lower part of the housing. This intermediate fixture includes means for retaining the support plate and a flexible gasket and is used to define a pressure chamber for the flexible diaphragm. The adapter can be fixedly but removably attached from the housing, as needed.

According to another preferred aspect of the invention, there is provided a blood pressure measuring device comprising:

a housing having a hollow interior;
a flexible diaphragm disposed in a lower portion of said housing interior, said diaphragm including a surface which deflects in response to pressure changes within the housing interior;
a movement mechanism having an input member and an output member, said output member being attached to indicating means;
a support plate having means for supporting said movement mechanism, wherein said diaphragm is positioned against a bottom surface of said support plate, said plate having a center opening sized for receiving said movement mechanism and means for aligning said input member relative to said diaphragm and wherein said diaphragm and said housing form a pressure chamber.

A perceived advantage of the present design is that the use of an O-ring or other flexible gasket forms the pressure chamber, along with the diaphragm and the housing. The use of the flexible gasket is an improvement over previous designs requiring soldering or other fixed attachments of the diaphragm, and requiring that similar materials be used for the diaphragm and support plate due to thermal expansion. Therefore, the mounting scheme of the present device is an improvement, particularly with regard to performance characteristics, such as linearity and repeatability, of an associated pressure sensing device.

These and other objects, features, and advantages will become apparent from the following Detailed Description of the Invention which should be read in conjunction with the accompanying drawings.

DETAILED DESCRIPTION OF THE INVENTION

The following description relates to specific embodiments of pressure sensing devices employing the concepts of the invention. It will be readily apparent to one of sufficient skill in the field that numerous modifications or variations can be made from the inventive concepts described herein. In addition, certain terms are used throughout the course of the discussion, such as "top", "upper", "bottom", "lower", etc to provide a frame of reference when using the accompanying drawings. These terms should not be construed to be overly limiting of the present invention. In addition, and though the embodiments relate to a specific pressure measuring device, a blood pressure gauge, it will also be readily apparent to one of skill in the field that other applications, such as barometers, force gauges, and the like, can utilize the inventive concepts described herein.

Figure 1:
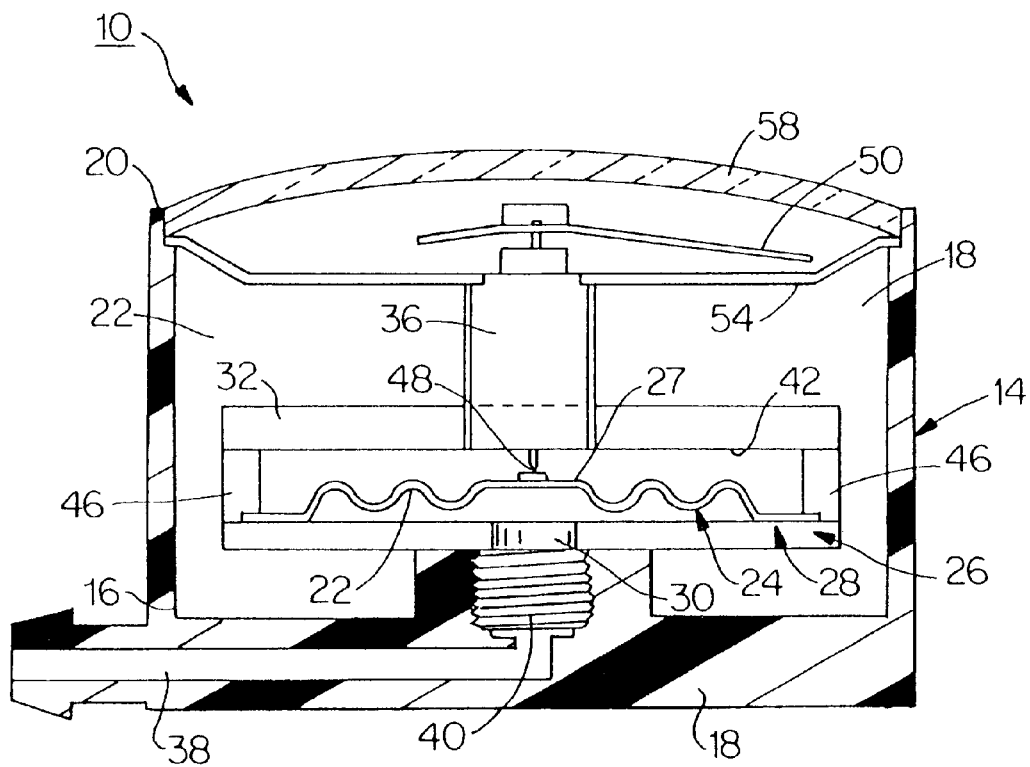
FIG. 1 is a partial sectional view of a pressure sensing device in accordance with the prior art.

Prior to discussing the present invention in detail and for background purposes, a brief summary is made of the blood pressure detecting device according to FIG. 1, partially shown. The device 10 includes a housing 14, which is a compact enclosure, having a substantially cylindrical or other convenient shape defined by a circumferential inner wall 16, a bottom wall 18, and an open top end 20. The interior 22 of the housing 14 is appropriately sized for retaining a number of components including a flexible diaphragm 24 comprising a thin cylindrical body made from a flexible material which is soldered or otherwise fixedly attached to the top surface 28 of a first supporting plate 26 made from a similar material. The first supporting plate 26 is a planar circular member including a center opening 30 which allows fluid communication between an air inlet 38 provided in the bottom wall 18 of the housing 14 and the interior of the flexible diaphragm 24. The air inlet 38 includes a vertically disposed center port 40 aligned with the center opening 30 of the first supporting plate 26. A second supporting plate, herein referred to as a bridge plate 32, is used for supporting a movement mechanism 36 of the device 10.

As noted, the diaphragm 24 is supported on the top surface 28 of the first supporting plate 26 and is positioned such that the diaphragm 24 is disposed outwardly; that is, toward the bottom surface 42 of the bridge plate 32. A set of standoffs 46 provide spacing between the plates 26, 32.

Air entering the inlet 38 passes through the vertically disposed port 40 and the center opening 30 of the first supporting plate 26, causing an exterior surface 27 of the diaphragm 24 to deflect against its fixed mount and impinge against an input member 48 of the movement mechanism 36. A needle or pointer element 50 supported at the top of the movement mechanism 36 is caused to rotate circumferentially relative to an indicating dial face 54 placed within a window or crystal 58 at the top of the housing 14, based on the axial movement of the input member 48.

Figure 2:
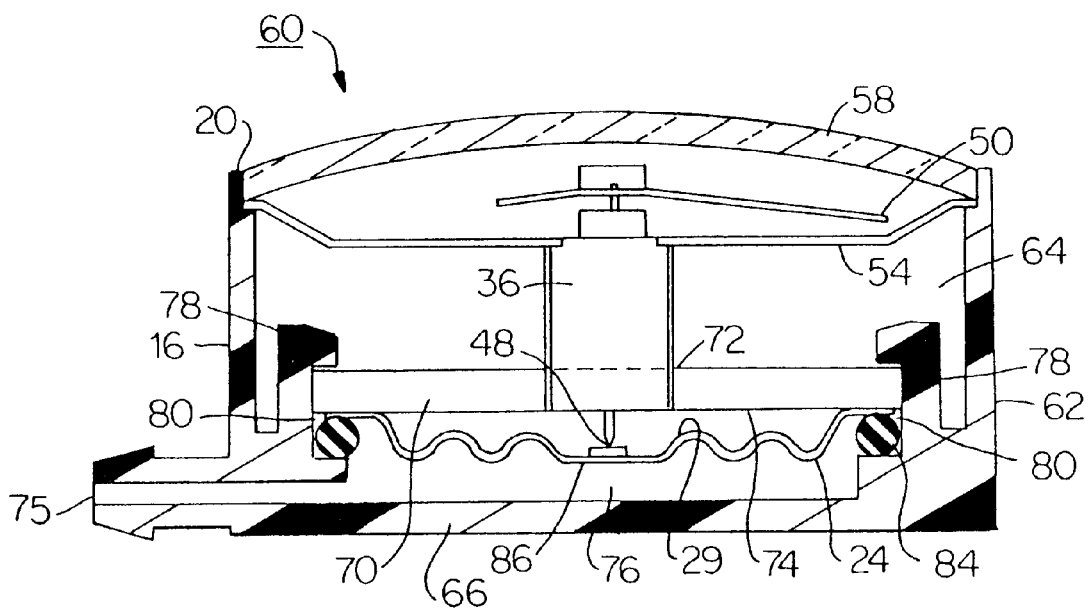
FIG. 2 is a partial sectional view of a pressure sensing device in accordance with a preferred embodiment of the present invention.

With the preceding background, reference is made to FIG. 2 which relates to a pressure sensing device 60 in accordance with a first preferred embodiment of the present invention. Similar components are labeled with the same reference numerals for the sake of clarity.

The device 60 includes a housing 62, similarly having a cylindrical or other suitable shape including a hollow interior 64 defined by a circumferential inner wall 16, a bottom wall 66, and an open top end 20. The hollow interior 64 is sized for containing a number of components as herein described, including a flexible expandable diaphragm 24, which is preferably nonfixedly mounted relative to the bottom surface 74 of a single circular support plate 70, as described in greater detail below.

Figure 3:
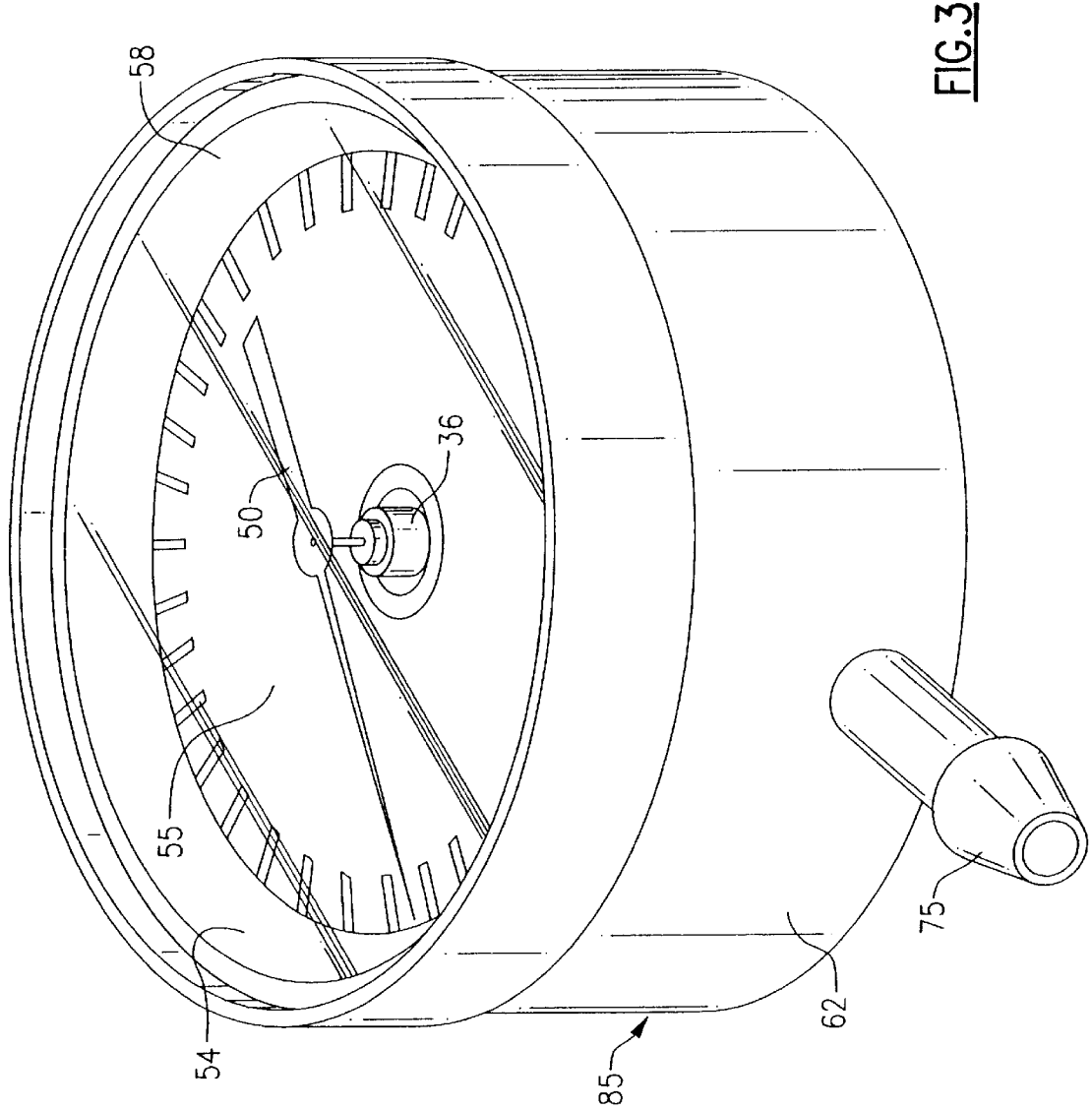
FIG. 3 is a partial top perspective view of a pressure sensing device in accordance with a second embodiment of the present invention.

A dial face 54 having a readable indicating portion 55, shown more clearly in FIG. 3, is supported within an upper portion of the housing interior 64 and a glass or clear plastic cover or window 58 is attached by known means to the open top end 20 of the housing 62. A pointer element 50 is integrally crimped or otherwise attached to the top or proximal end of a movement mechanism 36, the remaining end of which is attached fixedly through known means into a center opening 72 provided in the support plate 70. The movement mechanism 36 is positioned such that an input member 48 extends downwardly from the bottom surface 74 thereof and projects into the interior of the diaphragm 24. The interior surface 29 of the diaphragm 24 preferably includes a hard jeweled surface 86 aligned with the input member 48.

An air inlet 75 extends laterally into the lower portion of the interior 64 of the housing 62 into a defined pressure chamber 76 established between the housing interior 64 and the bottom surface 74 of the support plate 70. According to this embodiment, the support plate 70 is retained about its outer periphery within a plurality of arcuate slots 80, the slots each being provided in a plurality of circumferentially disposed retaining lugs 78 (only two of which are shown in FIG. 2) extending upwardly from the bottom wall 66 of the housing 62. The general shape of the support plate 70, shown in FIG. 4, includes a plurality of ears 73 on an outer periphery, each spaced similarly to the retaining lugs 78, allowing the support plate to be assembled to the housing 62 in a bayonet-type locking configuration.

According to the embodiment of FIG. 2, an O-ring 84 or other flexible gasket is fitted within the slot 80 along with the outer edge of the diaphragm 24, assembled with its exterior surface 27 pointing downwardly into the defined pressure chamber 76. The outer edge of the diaphragm 24 is therefore entirely supported between the flexible O-ring 84 and the bottom surface 74 of the support plate 70 within the slot 80.

In use, air enters the pressure chamber 76 through the inlet 75 and impinges against the exterior surface 27 of the supported diaphragm 24, wherein the O-ring 84 and the support plate 70 clamp and seal the edge of the diaphragm 24. The jeweled surface 86 located on the interior of the diaphragm 24 is thereby caused to move upwardly into contact with the input member 48 and cause an incremental movement of the pointer 50 in a known manner.

A number of benefits are immediately realized. First, and by inverting the diaphragm 24 there is no need for a second support plate given that there is sufficient space to define the expansion chamber 76 in the lower portion of the housing 60. Second, the support plate 70 can also support the movement mechanism 36, allowing the overall height dimension of the device to be reduced.

In addition, the nonfixed attachment of the diaphragm 24 using the flexible gasket 84, the support plate 70, and the housing 62, allows slippage of the components relative to one another resulting in improved response, as opposed to soldered or otherwise fixed mounting designs which mandate similar materials due to thermal expansion concerns.

Figure 4:
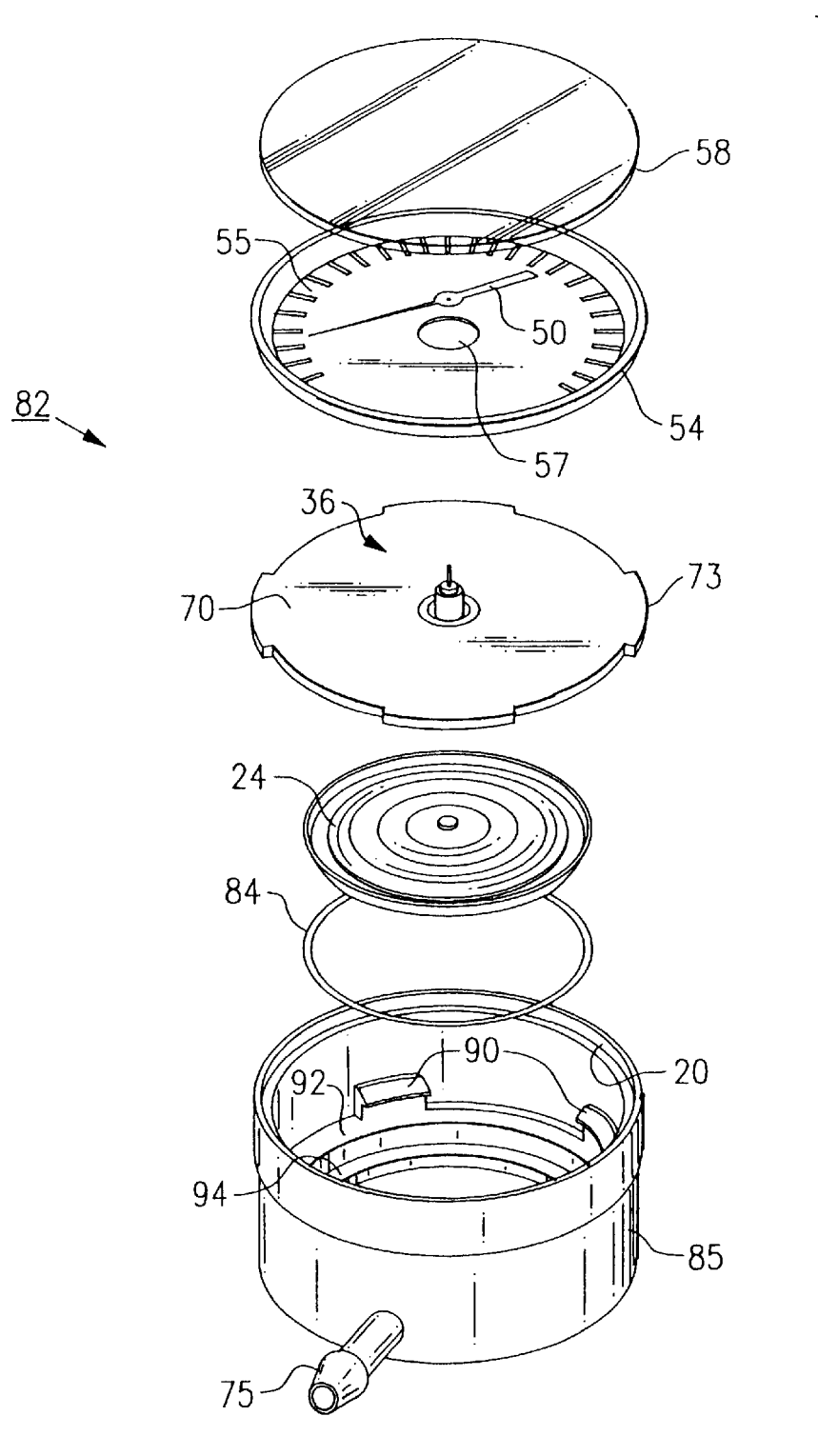
FIG. 4 is an exploded top perspective view of the device shown in FIG. 3.
Figure 5:
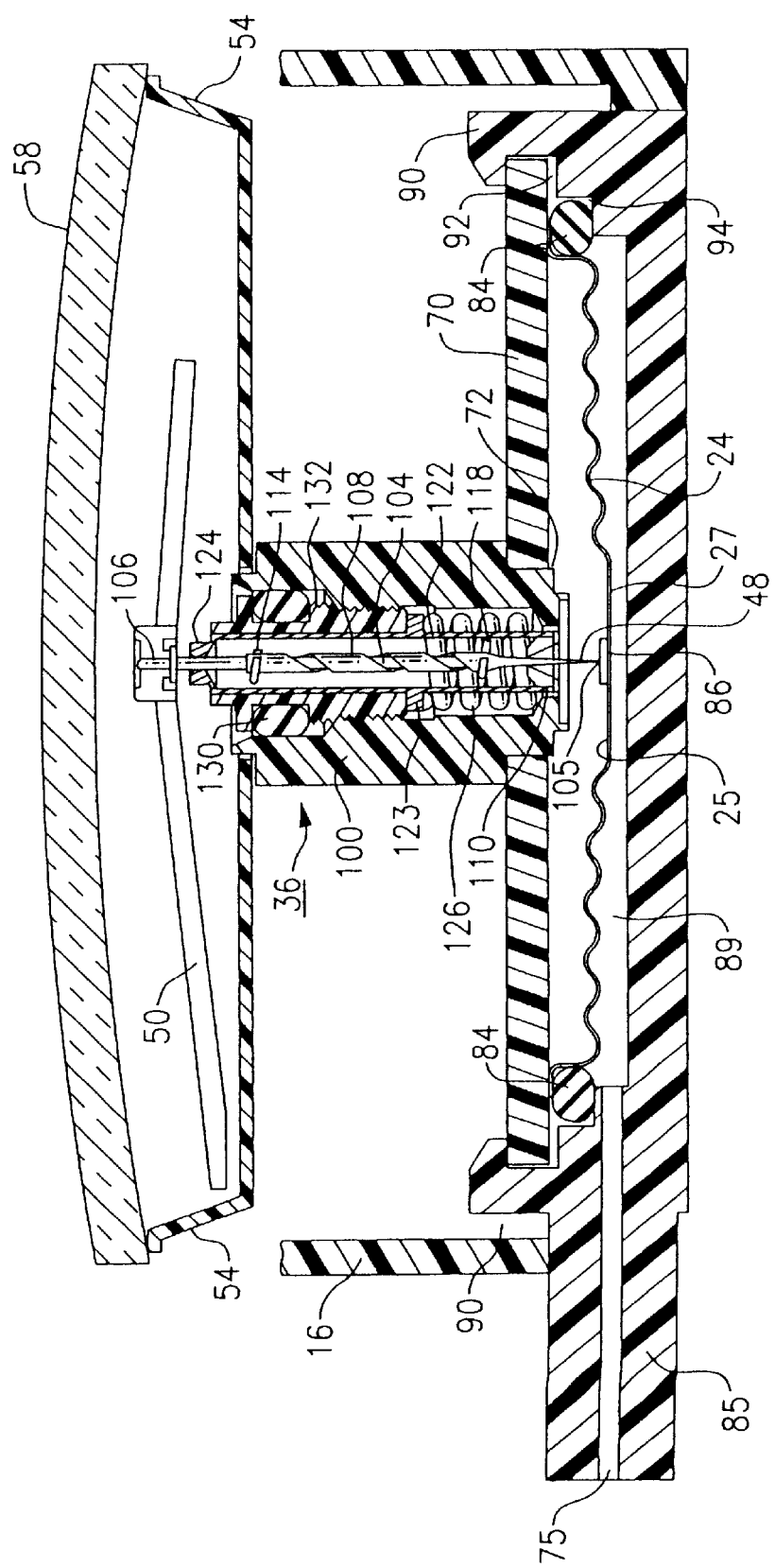
FIG. 5 is an enhanced sectional view of the device of FIGS. 2–4.

Turning now to FIGS. 3–5, a pressure sensing device 82 in accordance with a second embodiment of the present invention is herein described. As in the preceding, similar parts are herein labeled with the same reference numerals including the movement mechanism shown more completely in FIG. 5.

In brief and referring to FIG. 5, the movement mechanism 36 includes an elongate cylindrical pin member 104 acting as the input member 48 thereof having a distal end 105 and an opposite proximal end 106. The pin member 104 is typically fabricated from a hardened steel, though other suitable materials can easily be substituted.

A spring member 108 positioned over a portion of the cylindrical pin member 104 is attached at respective upper and lower ends to the cylindrical pin member and a bottom cap member 110. The spring member 108 is fabricated from a thin ribbon of a spring material, such as beryllium copper, which is helically wound into a cylindrical form, such that the cylindrical form is possessed in the free state of the spring member. The spring member 108 is relatively thin and has a suitable width dimension to avoid twisting and potential frictional interference with the cylindrical pin member 104 when operated, in the manner described below. The number of helical coils and size and thickness factors can be varied depending on the application.

A pair of cylindrical pins 114, 118 are provided for engaging attachment holes (not shown) at respective upper and lower ends of the spring member 108. Each pin 114, 118 is welded or otherwise attached to the exterior of the pin member 108 and the bottom cap member 110, respectively. Preferably, the attachment holes are oversized to introduce a sufficient amount of clearance.

A hollow cylindrical tubular sleeve 122 introduced over the coaxially arranged pin member 104 and the attached spring member 108 includes a bottom end which fits over portions of the bottom cap member 110, the cap member being fixedly attached in the lower end of a cartridge 100 containing the entirety of the movement mechanism 36. The tubular sleeve 122 includes a ring portion 123 acting as a collar for allowing a spring screw 132 to be fitted over an upper portion of the sleeve and a biasing spring 126 to be fitted over a lower portion thereof. A top cap member 124 extends through an opening 57, FIG. 4, of the dial face 54 through which the proximal end 106 of the shaft member 104 extends. The top cap member 124 also allows zero adjustment, if needed, to initially calibrate the pointer element 50 relative to the dial face 54. Additional details regarding the movement mechanism are described in greater detail in U.S. Ser. No. 08/972,573, incorporated above. The movement mechanism itself does not form the inventive concept of the present invention, except as indicated in the discussion.

Referring to FIGS. 4 and 5, and as in the preceding embodiment, the planar circular support plate 70 includes a plurality of ears 73 on the outer periphery thereof. In this embodiment, however, the ears 73 are secured in a bayonet-type of locking configuration within slots 92 formed in a corresponding number of retaining lugs 90 extending radially inward from the inner circumferential wall 16, FIG. 2, of the interior 88 of the housing 85, only partially shown, at a lower portion thereof. A rim 94 extending radially inward relative to the slots 92 extends over the inner circumference of the housing 85 and forms a step, sized to retain an O-ring 84. According to this embodiment, the diaphragm 24 is clamped between the O-ring 84 and the bottom surface 74 of the support plate 70 while the support plate is retained within the slot 92 of the retaining lugs 90.

An air inlet 75 extends into the housing interior and exits into the pressure chamber 89 defined by the lower interior of the housing 85, the bottom surface 74 of the support plate 70 and the O-ring 84.

For purposes of this embodiment, the cartridge 100 of the above movement mechanism 36 is assembled within the center opening 72 of the support plate 70 with the distal end 105 of the cylindrical pin member 104 extending from the bottom surface 74 and aligned with the jeweled surface 86 of the diaphragm interior.

As in the preceding embodiment, air entering the pressure chamber 89 through the air inlet 75 will impinge directly against the exterior surface 27 of the diaphragm 24. In response, the diaphragm 24 deflects upwardly against the support of the edges between the bottom surface 74 of the support plate 70 and compliant O-ring 84. The jeweled surface 86 provided on the interior surface 29 of the diaphragm 24 moves upwardly and engages the distal end 105 of the cylindrical pin member 104 of the movement mechanism 36 supported in the center opening 72 of the support plate 70. As a result, the cylindrical pin member 104 is caused to move axially in an upward direction, and causes expansion of the spiral spring member 108, causing circumferential displacement the pointer member 50, as described in previously incorporated U.S. Ser. No. 08/972,573.

Figure 6:
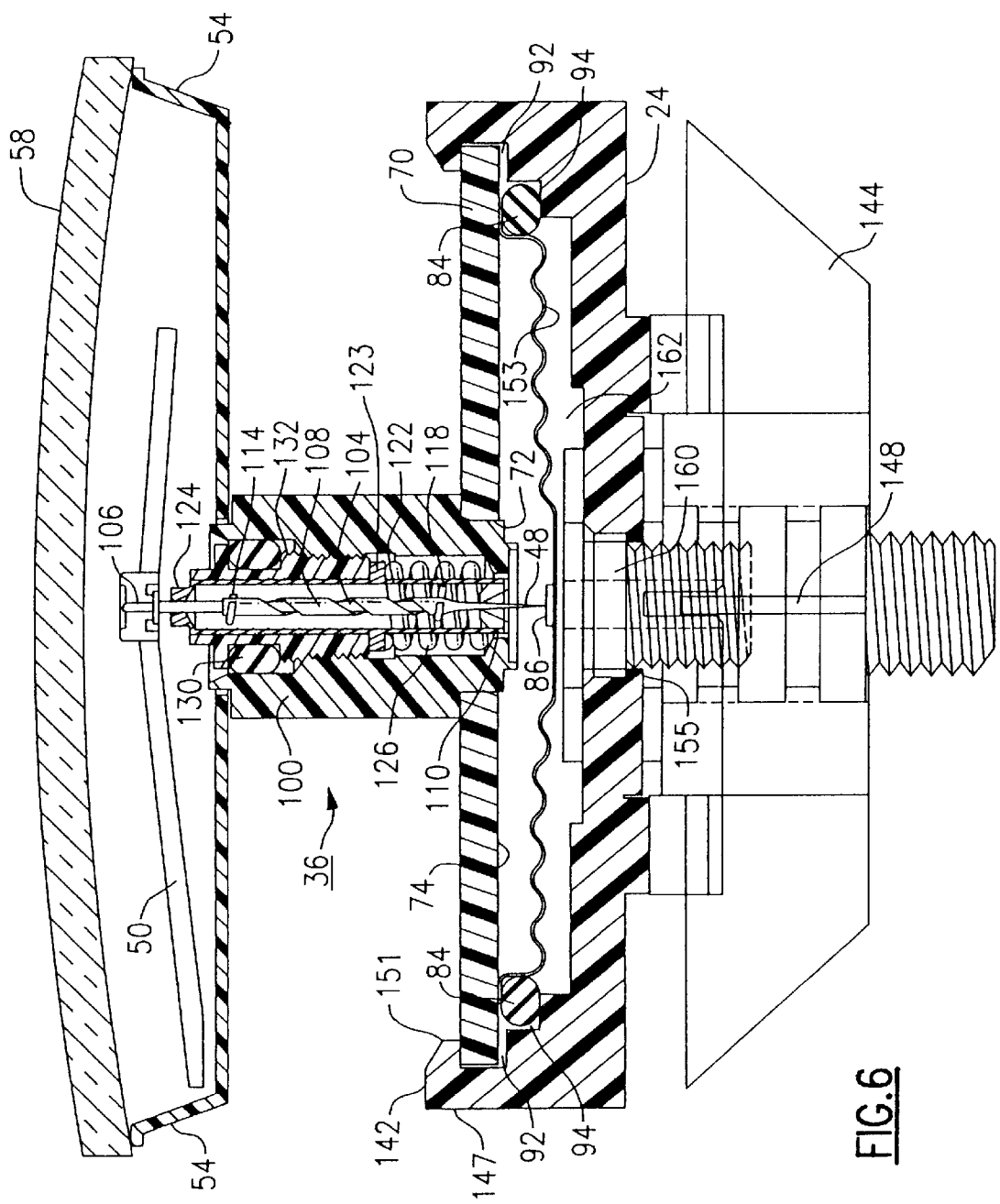
FIG. 6 is a partial sectional view of a pressure sensing device in accordance with a third embodiment of the present invention.

In some instances, it is desired to be able to retrofit the above design into existing gauge housings. FIG. 6 illustrates a third embodiment of the present invention utilizing an adapter 142 which can be fitted to a gauge housing 144 having a vertically disposed air inlet 148 extending through a vertically projecting threaded portion 160. As in the preceding, similar parts are labeled with the same reference numerals for the sake of clarity.

In this particular embodiment, the adapter 142 is a cylindrical cup-like member having an interior wall 147, an open top end 151 and a bottom wall 153. The adapter 142 includes a plurality of retaining lugs 90 adjacent the open top end 151, each lug having an arcuate slot 92 sized for retaining the ears 73, FIG. 4, of a support plate 70, in the manner previously described. The adapter 142 further includes a circumferential rim 94 immediately beneath the slots 92 and directed radially inward of the slots 92, the rim being used for retaining an O-ring 84. As in the preceding, a flexible diaphragm 24 is supported at its outer periphery between the O-ring 84 and the bottom surface 74 of the support plate 70 attached in a bayonet-type manner to the slots 92 of the adapter 142. Spacing between the rim 94 and the bottom wall 153 of the adapter 142 creates a pressure chamber 162.

A movement mechanism 36, having each of the components previously discussed with respect to FIG. 5, is threaded into the center opening 72 of the support plate 74 and is positioned such that the distal end 105 of the cylindrical pin member 104 is aligned with a hard jeweled surface 86 provided in the interior of the assembled diaphragm 24.

The bottom wall 153 of the adapter 142 includes a center opening 155 which is aligned with the vertically disposed air inlet 148 and is sized to be threaded onto the projecting threaded portion 160.

In use, the adapter 142 is threaded into place to the gauge housing 144 after the O-ring 84, the diaphragm 24 and the support plate 70 have been assembled to the adapter as shown in FIG. 6. The movement mechanism 36 is assembled to the support plate 70 through the center opening 72. Air enters the pressure chamber 162 of the adapter 142 through the air inlet 148 and causes deflection of the supported diaphragm 24, as previously described, into contact with the input member 48 of the movement mechanism 36 and corresponding movement of the pointer element 50.

PARTS LIST FOR FIGS. 1–6

10 gauge mechanism
14 housing
16 circumferential inner wall
18 bottom wall
20 open top end
22 interior
24 diaphragm
26 supporting plate
27 exterior surface
28 top surface
29 interior surface
30 center opening
32 bridge plate
36 movement mechanism
38 air inlet
40 vertically disposed port
42 bottom surface
46 standoffs
48 input member
50 needle or pointer element
54 dial face
55 indicating portion
58 window
60 housing
64 hollow interior
66 bottom wall
70 circular support plate
72 center opening
73 ears
74 bottom surface
75 air inlet
76 pressure chamber
78 retaining lugs
80 slots
82 pressure sensing device
84 O-ring
85 housing
86 jeweled surface
88 interior
89 pressure chamber
90 retaining lugs
91 bottom wall
92 slot
94 rim
104 elongate pin member
105 distal end
106 proximal end
108 spring member
110 bottom cap member
114 cylindrical pin
118 cylindrical pin
122 sleeve
123 ring portion
124 top cap member
126 biasing spring
130 O-ring
132 spring screw
142 adapter
144 housing
147 interior wall
148 air inlet
151 open top end
153 bottom wall
155 center opening
160 threaded portion
162 pressure chamber These and other variations and modifications will be readily apparent to one of ordinary skill in the field as evidenced from the following claims which better define the scope of the present invention.

We claim:

1. A pressure sensing device comprising:

a housing having a hollow interior and including at least one inlet disposed in a lower portion thereof;

a source of fluid in communication with said at least one inlet;

a flexible diaphragm adjacently disposed relative to said at least one inlet, said diaphragm having a surface responsive to the flow of fluid entering and leaving said housing through said at least one inlet;

a movement mechanism having an axial input member having a first end disposed adjacently to the flexible expanding surface of said diaphragm and a second end attached to indicating means provided in an upper portion of said housing; and means for supporting said flexible diaphragm and said movement mechanism within the interior of said housing, said supporting means including a support plate having a bottom side and a top side, wherein said diaphragm is disposed adjacent the bottom side of said support plate, and wherein the interior of said housing and said diaphragm define a chamber sized for allowing movement of said flexible diaphragm relative to said axial input member, said movement mechanism further including a spring member helically wound about a portion of said input member, said spring member having one end attached to said input member and a second end attached to a tubular sleeve enclosing said spring member and at least an axial portion of said input member.

2. A pressure sensing device according to claim 1, wherein said flexible diaphragm is nonfixedly attached to the housing.

3. A pressure sensing device according to claim 2, wherein said diaphragm supporting means includes a flexible gasket, wherein the outer periphery of said diaphragm is retained between said flexible gasket and the bottom side of said support plate.

4. A pressure sensing device according to claim 3, wherein said flexible gasket is an O-ring which forms a seal for said chamber.

5. A pressure sensing device according to claim 4, wherein said chamber is defined by said diaphragm, said housing and said O-ring.

6. A pressure sensing device according to claim 2, wherein said support plate and said diaphragm are made from dissimilar materials.

7. A pressure sensing device according to claim 1, wherein said support plate includes a center opening sized for retaining said movement mechanism and means for positioning an input member of said movement mechanism in relation to said diaphragm.

8. A pressure sensing device according to claim 1, wherein said supporting means includes a plurality of circumferentially spaced retaining lugs disposed from said housing, said plate including a plurality of spaced ears for engaging said retaining lugs.

9. A blood pressure measuring device comprising:

a housing having a hollow interior and including at least one inlet disposed in a lower portion thereof;

a source of fluid in communication with said at least one inlet;

a flexible diaphragm adjacently disposed relative to said at least one inlet, said diaphragm having a surface responsive to the flow of fluid entering and leaving said housing through said at least one inlet;

a movement mechanism having an axial input member having a first end disposed adjacently to the flexible expanding surface of said diaphragm and a second end attached to indicating means in an upper portion of said housing; and means for supporting said flexible diaphragm and said movement mechanism within the interior of said housing, said supporting means including a single support plate having a bottom side and a top side, wherein said diaphragm is disposed adjacent the bottom side of said support plate, and wherein the lower part of said housing and said diaphragm define a chamber sized for allowing movement of said flexible diaphragm relative to said axial input member, said movement mechanism further including a spring member helically wound about a portion of said input member, said spring member having one end attached to said input member and a second end attached to a tubular sleeve enclosing said spring member and at least an axial portion of said input member.

10. A blood pressure measuring device according to claim 9, wherein said flexible diaphragm is nonfixedly attached to the housing.

11. A blood pressure measuring device according to claim 10, wherein said diaphragm supporting means includes a flexible gasket, wherein the outer periphery of said diaphragm is retained between said flexible gasket and the bottom side of said support plate.

12. A blood pressure measuring device according to claim 11, wherein said flexible gasket is an O-ring which forms a seal for said chamber.

13. A blood pressure measuring device according to claim 12, wherein said chamber is defined by said diaphragm, said housing and said O-ring.

14. A blood pressure measuring device according to claim 10, wherein said support plate and said diaphragm are made from dissimilar materials.

15. A blood pressure measuring device according to claim 9, wherein said support plate includes a center opening sized for retaining said movement mechanism and means for positioning an input member of said movement mechanism in relation to said diaphragm.

16. A blood pressure measuring device according to claim 9, wherein said supporting means includes a plurality of circumferentially spaced retaining lugs disposed from said housing, said plate including a plurality of spaced ears for engaging said retaining lugs.

* * * * *